(12) United States Patent
Dale et al.

(10) Patent No.: US 8,435,960 B2
(45) Date of Patent: May 7, 2013

(54) DEVICES FOR IMPROVED WOUND MANAGEMENT

(75) Inventors: Roderic M. K. Dale, Wilsonville, OR (US); Steven L. Gatton, Lake Oswego, OR (US); Amy Arrow, Bethel, ME (US)

(73) Assignee: Lakewood-Amedex, Inc., Lakewood Ranch, FL (US)

( * ) Notice: Subject to any disclaimer, the term of this patent is extended or adjusted under 35 U.S.C. 154(b) by 0 days.

(21) Appl. No.: 12/130,405

(22) Filed: May 30, 2008

(65) Prior Publication Data

US 2009/0092659 A1    Apr. 9, 2009

Related U.S. Application Data

(60) Continuation of application No. 10/644,969, filed on Aug. 21, 2003, now abandoned, which is a division of application No. 09/281,858, filed on Mar. 31, 1999, now Pat. No. 6,627,215, which is a continuation-in-part of application No. 09/222,009, filed on Dec. 30, 1998, now Pat. No. 6,211,349.

(51) Int. Cl.
   *A01N 43/04*   (2006.01)
   *C12N 15/63*   (2006.01)
   *C07H 21/02*   (2006.01)
   *C07H 21/04*   (2006.01)
   *C07H 19/00*   (2006.01)

(52) U.S. Cl.
   USPC ........ 514/44; 536/23.1; 536/24.1; 536/24.33; 536/28.2; 435/455

(58) Field of Classification Search ................... 435/455; 514/44; 536/23.1, 24.1, 24.33, 28.2
   See application file for complete search history.

(56) References Cited

U.S. PATENT DOCUMENTS

| | | | |
|---|---|---|---|
| 4,105,782 A | 8/1978 | Yu et al. | |
| 4,377,159 A | 3/1983 | Hansen | |
| 4,414,970 A | 11/1983 | Berry | |
| 4,421,769 A | 12/1983 | Dixon et al. | |
| 4,464,392 A | 8/1984 | Bailey et al. | |
| 4,655,202 A | 4/1987 | Potter et al. | |
| 4,672,956 A | 6/1987 | Potter et al. | |
| 4,867,821 A | 9/1989 | Morgan | |
| 4,897,355 A | 1/1990 | Eppstein et al. | 435/240.2 |
| 4,908,209 A | 3/1990 | McIntosh, Jr. et al. | |
| 5,030,659 A | 7/1991 | Bansemir et al. | |
| 5,153,000 A | 10/1992 | Chikawa et al. | |
| 5,153,230 A | 10/1992 | Jaffery | |
| 5,294,533 A | 3/1994 | Lupski et al. | |
| 5,360,797 A | 11/1994 | Johnson et al. | |
| 5,376,067 A | 12/1994 | Daneshvar | |
| 5,420,330 A | 5/1995 | Brush | |
| 5,499,966 A | 3/1996 | Bulley et al. | |
| 5,510,104 A | 4/1996 | Allen | |
| 5,603,915 A | 2/1997 | Nelson et al. | |
| 5,652,266 A | 7/1997 | Bobier-Rival et al. | |
| 5,681,829 A | 10/1997 | Tempesta et al. | |
| 5,685,833 A | 11/1997 | Turngren | |
| 5,692,937 A | 12/1997 | Zhang | |
| 5,718,674 A | 2/1998 | Penrose | |
| 5,733,545 A | 3/1998 | Hood, III | |
| 5,739,309 A | 4/1998 | Dattagupta et al. | |
| 5,747,256 A | 5/1998 | Yan et al. | |
| 5,763,468 A | 6/1998 | Barranx et al. | |
| 5,767,054 A | 6/1998 | Sprugel et al. | |
| 5,792,092 A | 8/1998 | Turngren | |
| 5,830,140 A | 11/1998 | Dillinger et al. | |
| 5,843,998 A | 12/1998 | Song et al. | |
| 6,211,162 B1 | 4/2001 | Dale et al. | |
| 6,211,349 B1 | 4/2001 | Dale et al. | |
| 6,627,215 B1 | 9/2003 | Dale et al. | |
| 7,176,191 B2 | 2/2007 | Dale et al. | |
| 7,868,162 B2 | 1/2011 | Dale | |
| 2002/0032164 A1 | 3/2002 | Dale et al. | 514/44 |
| 2005/0025815 A1 | 2/2005 | Dale et al. | |
| 2007/0053971 A1 | 3/2007 | Dale | |
| 2009/0092659 A1 | 4/2009 | Dale et al. | |

FOREIGN PATENT DOCUMENTS

| | | |
|---|---|---|
| CN | 1687100 A | 10/2005 |
| EP | 0018492 A1 | 11/1980 |
| EP | 148709 A1 | 7/1985 |
| EP | 1140965 B1 | 10/2001 |
| EP | 1169046 B1 | 1/2002 |
| JP | 5115637 A | 5/1993 |
| WO | WO-8901023 A1 | 2/1989 |
| WO | WO-9014074 A1 | 11/1990 |
| WO | WO-9116024 A1 | 10/1991 |
| WO | WO-9117424 A1 | 11/1991 |
| WO | WO-9220697 A1 | 11/1992 |
| WO | WO-9408563 A1 | 4/1994 |
| WO | WO-9415619 A1 | 7/1994 |
| WO | WO-9629399 A1 | 9/1996 |
| WO | WO-9719593 A1 | 6/1997 |
| WO | WO-9803533 A1 | 1/1998 |
| WO | WO-9823294 A1 | 6/1998 |
| WO | WO-0040591 A1 | 7/2000 |
| WO | WO-0057890 A1 | 10/2000 |
| WO | WO-02080668 A2 | 10/2002 |
| WO | WO-02089581 A1 | 11/2002 |
| WO | WO-2008133704 A2 | 11/2008 |

OTHER PUBLICATIONS

Archer et al., *Antimicrob. Agents Chemother.* 38:2231-2237 (1994).

(Continued)

*Primary Examiner* — Shin-Lin Chen
(74) *Attorney, Agent, or Firm* — Mintz Levin Cohn Ferris Glovsky and Popeo, P.C.; Ingrid A. Beattie

(57) ABSTRACT

The present invention provides devices and compositions for the management of infection of topical lesions, each of the devices and compositions containing protonated/acidified nucleic acids either on its surface, or integrated into the device. These modified nucleic acids are effective as bactericidal and/or bacteriostatic agents without regard to the class of bacteria, so are especially useful when diagnosis is difficult or when multiple infectious organisms are present. The antibiotic activity of nucleic acids of the invention is not dependent on either the specific sequence of the nucleic acid or the length of the nucleic acid molecule. The nucleic acids used in the invention are protonated/acidified to give a pH when dissolved in water of less than pH 7 to about 1, more preferably less than pH 4.5 to about 1, and even more preferably less than pH 2 to about 1.

5 Claims, 2 Drawing Sheets

OTHER PUBLICATIONS

Bennett, *Antisense Res. Devel.* 3:235-241 (1993).
Burns et al., "Clinical Manifestations and Treatment of Pulmonary Infections in Cystic Fibrosis", *Advances in Pediatric Infectious Diseases*, 8:53-67 (1993).
Cameron, *British Journal of Theatre Nursing* 7(5):5-7 (Aug. 1997).
Center for Disease Control, "Update: Mortality Attributable to HIV Infection Among Persons Aged 25-44 Years—Unites States, 1994", *Morbidity and Mortality Weekly Report*, 45(6):121-144 (1996).
Cohen et al., "High-performance liquid chromatography and capillary gel electrophoresis as applied to antisense DNA", *J. Chrom.*, 638:293-301 (1993).
Cohen, Oligodeoxynucleotides; *Antisense Inhibitors of Gene Expression*, Boca Raton, FL, CRC Press. (1989).
Crooke, Antisense Nucleic Acid and Antisense RNA: Novel Pharmacological and Therapeutic Agents, B. Weiss ed., CRC Press Boca Raton, FL., p. 17 (1997).
Dale et al., "Therapeutic Efficacy of 'Nubiotics' against Burn Wound Infection by *Pseudomonas aeruginosa*", *Antimicrobial Agents Chemotherapy*, 48(8):2918-2923 (2004).
Eck et al., Goodman & Gilman's The Pharmacological Basis of Therapeutics, Ninth Editiion, McGraw-Hill, New York, p. 77-101, 1996.
Freelander, Hosp Med (Jun. 1998) 59(6):484-7.
Goth, Medical Pharmacology: Principles and Concepts, The C.V. Mosby Company, Saint Louis, MO..(1974).
Gould et al., "Does Placebo Lower Blood-Pressure?" *Lancet*, 22:1377-81 (1981).
Heidenreich et al., Molecular Medicine Today, vol. 1(3), p. 128-133, 1995.
Hoke et al., *Nucl. Acids Res.* 19:5743 (1991).
Hughes et al., *Pharmaceutical Research* 12:817 (1995).
Jones et al., *Nurs Stand* 12(39):47-52 (Jun. 17-23, 1998).
Krieg et al., *Nature* 374:546-549 (1995).
Kristinsson, *Microb. Drug Resistance* 1(2):121 (1995).
LaPlanche et al., "Phosphorothioate-modified oligodeoxyribonucleotides. III. NMR and UV spectroscopic studies of the $R_p$-$R_p$, $S_p$-$S_p$, and $R_p$-$S_p$ duplexes, [d($GG_sAATTCC$)]2, derived from diastereomeric O-ethyl phosphorothioates", *Nuc. Acid. Res.*, 14(22):9081-9093 (1986).
Levy et al., "Bioactivity of Gentamicin in Purulent Sputum from Patients with Cystic Fibrosis or Bronchiectasis: Comparison with Activity in Serum", *J. Infect. Dis.*, 148(6):1069-1076 (1983).
Mastrangelo et al., *Seminars in Oncology*, 23 (1):4-21 (Feb. 1996).
McCutcheon's, vol. 2 Functional Materials, North American Edition, 137-168 (1992).
Pennington, J. E., "Penetration of Antibiotics into Respiratory Secretions", *Rev. Infect. Dis.*, 3(1):67-73 (1981).
Reed et al., "A Simple Method of Estimating Fifty Percent Endpoints" *Amer. J. Hyg.*, 27(3):493-497 (1938).
Snoeck, et al., "(S)-1-(3-Hydroxy-2-Phosphonylmethoxypropyl)Cytosine, a Potent and Selective Inhibitor of Human Cytomegalovirus Replication", *Antimicrobial Agents and Chemotherapy*, 32(12):1839-1844 (1988).
Spotnitz et al., *Surg Clin North Am* 77(3):651-69 (Jun. 1997).
Staley et al., *Adv Wound Care* 10(2):39-44 (Mar.-Apr. 1997).
Stec et al., "Automated Solid-Phase Synthesis, Separation, and Stereochemistry of Phosphorothioate Analogues of Oligodeoxyribonucleotides", *J. Am. Chem. Soc.*, 106:6077-6079 (1984).
Stec et al., "Solid-Phase Synthesis, Separation, and Stereochemical Aspects of P-Chiral Methane- and 4,4'-Dimethoxytriphenylmethanephosphonate Analogues of Oligodeoxyribonucleotides", *J. Org. Chem.*, 50(20):3908-3913 (1985).
Stec et al., "Reversed-Phase High-Performance Liquid Chromatographic Separation of Diastereomeric Phosphorothioate Analogues of Oligodeoxyribonucleotides and Other Backbone-Modified Congeners of DNA", *J. Chromatog.*, 326:263-280 (1985).
T.W. Graham Solomans, Organic Chemistry, John Wiley and Sons, Inc., New York, 6th ed. pp. 937-971 (Jul. 1998).
The Merck Index, 12th edition, pp. 1490-1491; 763-764 (1996).
Verma et al., *Nature*, 389:239-242 (Sep. 1997).
Wenninger et al., CTFA Cosmetic Ingredient Handbook, Second Edition, The Cosmetic, Toiletry and Fragrance Association, Washington, D.C., pp. 572-575 and 580 (1992).
Woodford et al., *J. Antimicrob. Chemother.* 35:179-184 (1995).
Wu-Pong, S., *Pharmaceutical Technology*, Oct. 1994, p. 102, 104, 106, 108, 110-112, 114 (1994).
Yamamoto et al., *Antisense Res. Devel.* 4:119-122 (1994).
Zabransky et al., *J. Clin. Microbiol.* 3(4):791-793 (1995).
Zimmer et al., *Biopolymers*, 6(4):563-574 (1968).
Office Action for Japanese Application No. 2000-592299 dated Aug. 18, 2010.
Sarocchi et al., "Influence of DNA Acidification on DNA Premelting and Template Properties", *Eur. J. Biochem.*, 65:587-599 (1976).
Jernigan et al., eds., "Defining the Public Health Impact of Drug-Resistant *Streptococcus pneumoniae*", *MMWR*, 45(RR-1):1-26 (1996).
Lu et al. "Synthetic Analogues of Irlbacholine: A Novel Antifungal Plant Metabolite Isolated From *Irlbachia alata.*" *J. Nat. Prod.* 62.6(1999):824-828.
Dale et al. "Therapeutic Efficacy of Aerosolized Liposome-Encapsulated Nubiotic Against Pulmonary *Pseudomonas aeruginosa* Infection." *Therapy.* 4.4(2007):441-449.

Fig 1. Establishment of burn wound infection by subcutaneous and topical administration of *Pseudomonas aeruginosa*.
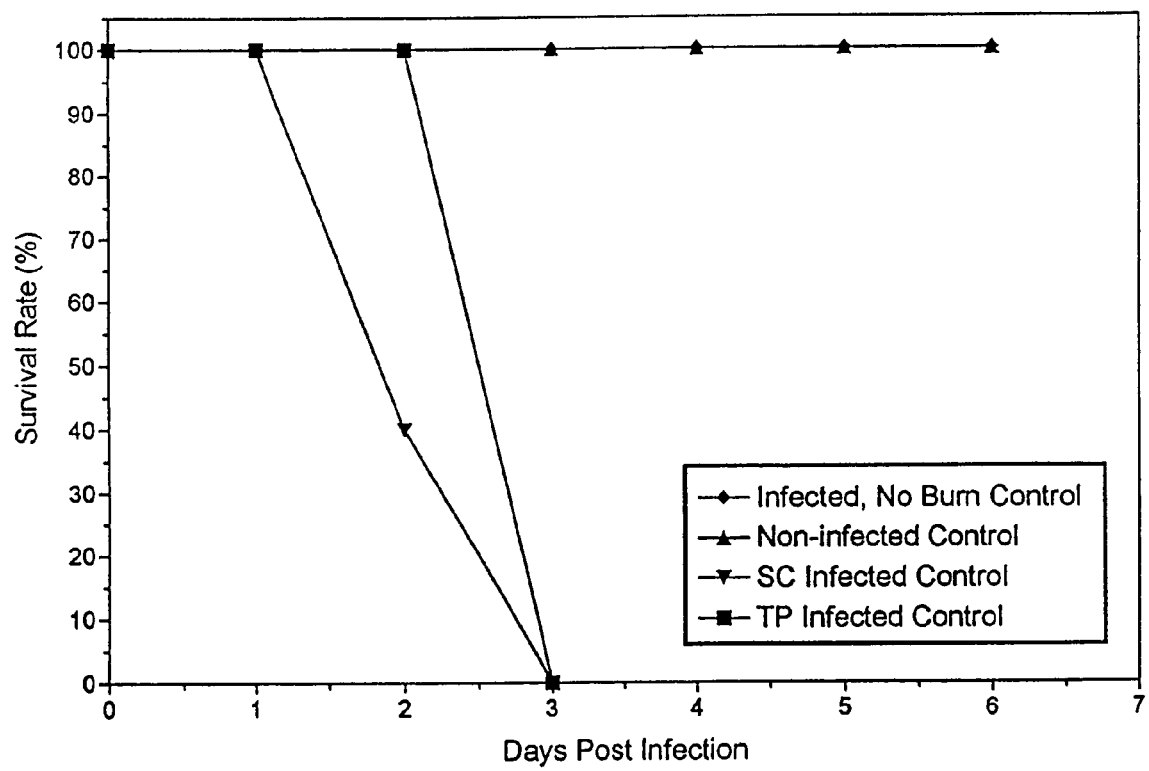

Fig 2. Optimization of routes of nubiotic administration for the treatment of burn wound infection.
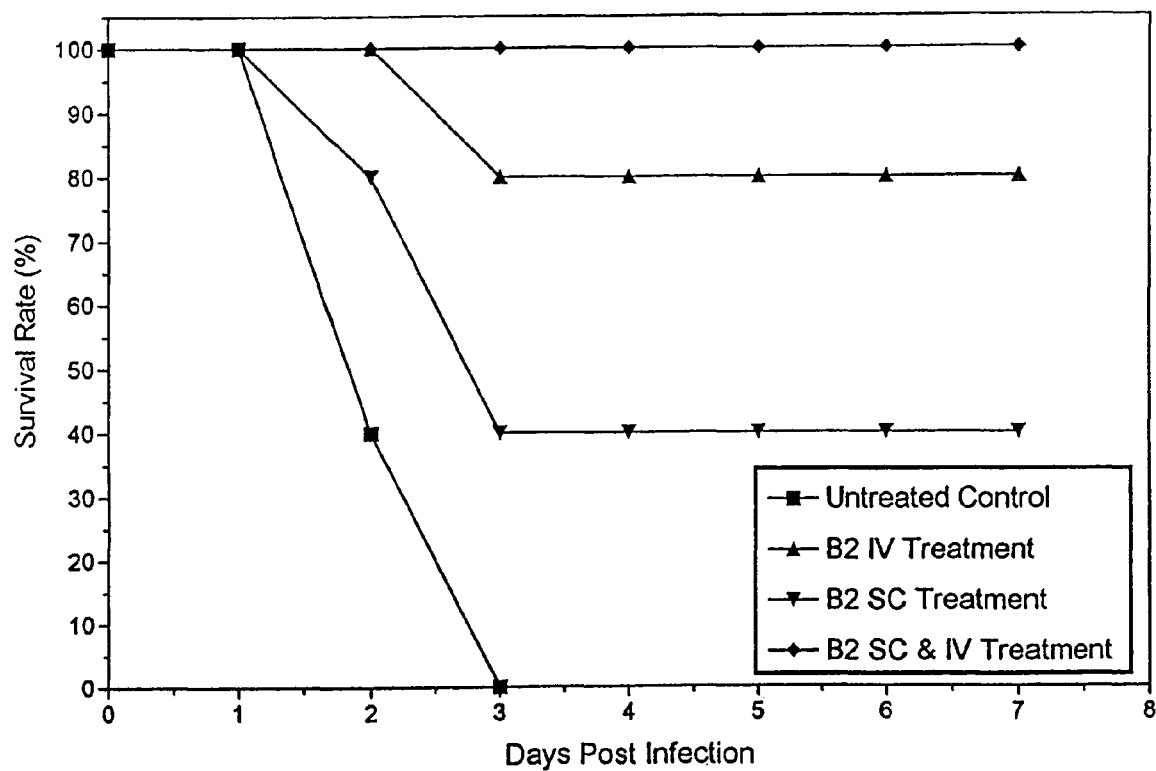

SEQUENCE LISTING

<160> NUMBER OF SEQ ID NOS: 9

<210> SEQ ID NO 1
<211> LENGTH: 9
<212> TYPE: DNA
<213> ORGANISM: Artificial Sequence
<220> FEATURE:
<223> OTHER INFORMATION: Chemically synthesized oligonucleotide

<400> SEQUENCE: 1 cgccattgg                                                                9

<210> SEQ ID NO 2
<211> LENGTH: 6
<212> TYPE: DNA
<213> ORGANISM: Artificial Sequence
<220> FEATURE:
<223> OTHER INFORMATION: Chemically synthesized oligonucleotide -continued

```
<400> SEQUENCE: 2 cgccat                                                              6

<210> SEQ ID NO 3
<211> LENGTH: 12
<212> TYPE: DNA
<213> ORGANISM: Artificial Sequence
<220> FEATURE:
<223> OTHER INFORMATION: Chemically synthesized oligonucleotide

<400> SEQUENCE: 3
acgcgccatt gg                                                      12

<210> SEQ ID NO 4
<211> LENGTH: 21
<212> TYPE: DNA
<213> ORGANISM: Artificial Sequence
<220> FEATURE:
<223> OTHER INFORMATION: Chemically synthesized oligonucleotide

<400> SEQUENCE: 4
ggaacgcgcc attggtatat c                                            21

<210> SEQ ID NO 5
<211> LENGTH: 12
<212> TYPE: DNA
<213> ORGANISM: Artificial Sequence
<220> FEATURE:
<223> OTHER INFORMATION: Chemically synthesized oligonucleotide

<400> SEQUENCE: 5
aaaaaaaaaa aa                                                      12

<210> SEQ ID NO 6
<211> LENGTH: 12
<212> TYPE: DNA
<213> ORGANISM: Artificial Sequence
<220> FEATURE:
<223> OTHER INFORMATION: Chemically synthesized oligonucleotide

<400> SEQUENCE: 6
uuuuuuuuuu uu                                                      12

<210> SEQ ID NO 7
<211> LENGTH: 12
<212> TYPE: DNA
<213> ORGANISM: Artificial Sequence
<220> FEATURE:
<223> OTHER INFORMATION: Chemically synthesized oligonucleotide

<400> SEQUENCE: 7
gggggggggg gg                                                      12

<210> SEQ ID NO 8
<211> LENGTH: 12
<212> TYPE: DNA
<213> ORGANISM: Artificial Sequence
<220> FEATURE:
<223> OTHER INFORMATION: Chemically synthesized oligonucleotide

<400> SEQUENCE: 8
cccccccccc cc                                                      12
```

```
<210> SEQ ID NO 9
<211> LENGTH: 12
<212> TYPE: DNA
<213> ORGANISM: Artificial Sequence
<220> FEATURE:
<223> OTHER INFORMATION: Chemically synthesized oligonucleotide

<400> SEQUENCE: 9
acgcgccatt at                                                              12
```

DEVICES FOR IMPROVED WOUND MANAGEMENT

This application is a continuation of U.S. Ser. No. 10/644,969, filed Aug. 21, 2003 (abandoned), which is a divisional of U.S. Ser. No. 09/281,858, filed Mar. 31, 1999 (now U.S. Pat. No. 6,627,215),which is a continuation-in-part of our earlier filed application Ser. No. 09/222,009, filed Dec. 30, 1998 (now U.S. Pat. No. 6,211,349), to which we claim priority under 35 U.S.C. §120, each of which is incorporated herein by reference in its entirety.

INCORPORATION BY REFERENCE

The contents of the text file named "38950-503C02US_ST25.txt", which was created on Aug. 17, 2011 and is 3 KB in size, are hereby incorporated by reference in their entirety.

FIELD OF THE INVENTION

This invention relates generally to devices for promoting closure, healing, and/or prevention of infection in burn wounds, ulcers, donor sites, bites and other shallow wounds. More particularly, this invention pertains to such devices that have a broad spectrum antibiotic effect.

BACKGROUND OF THE INVENTION

The skin is an essential component of the nonspecific immune system and functions as a first barrier to pathogenic infection. Breaches in the skin, i.e., wounds, predispose the patient to infection. Thermal burns cause massive destruction of the integument as well as suppression of humoral and cellular immunity, enabling opportunistic organisms that do not generally infect a healthy person to infect a burn victim, both topically and systemically. Scratches, bites and ulcers also cause infection by allowing the introduction of microorganisms into deeper, susceptible tissues.

Each year, approximately 2.4 million Americans are burned. Physicians treat about 650,000 of the burn victims, 75,000 of these patients require hospitalization, and 12,000 die of burns. One million people each year sustain substantial temporary or permanent disabilities resulting from burn injuries. Infectious complications are the leading cause of morbidity and mortality in serious burn injury, with approximately 10,000 patients in the U.S. dying of burn-related infections each year. When skin is damaged or missing due to burns, trauma or toxic injury, the mechanical functions of the skin must be replaced promptly to provide an environment that will optimize cellular regeneration and minimize the chance for sepsis. During this healing process, systemic immunosuppression is induced, placing the patient at greater risk for infection. Burns also predispose the affected area to infection by damaging the protective barrier function of the skin, thus allowing the entry and colonization of opportunistic organisms.

An ultimate goal of burn wound management is closure and healing of the wound. One way in which wound healing is promoted is the use of dressings to cover the wound site. An ideal dressing is one that flexibly covers the wound site and provides a barrier to infectious organisms and an environment that promotes the healing process. A preferred environment is one similar to the patient's own skin in providing a moisture retaining, germ resistant covering while possibly stimulating the healing. Although biological dressings, e.g., porcine xenografts, have been the dressing of choice since the early 1960's, new synthetic dressings are being introduced that have the additional benefit of being sterile. Both biological and synthetic dressings serve as temporary coverages for wounds and essentially all provide a barrier that aids in healing.

Burn wound healing has traditionally been augmented by the use of topical antibiotics. Currently, the most common antimicrobial agents used for burn victims are silver sulfadiazene cream, mafenide acetate cream, and silver nitrate, which dramatically decrease the bacterial burden of burn wounds and consequently decrease the rate of infection. These compounds, although effective, have limitations. Silver sulfadiazene is often used initially, but its value is often limited by bacterial resistance. Mafenide acetate is more broad spectrum in effect but it has negative side effects such as metabolic acidosis and hypersensitivity.

Other wounds can also be problematic for the treatment of antibiotic infection, especially wounds that are more likely to expose a subject to infectious agents (e.g., an animal bite), or wounds that are deep and/or difficult to access (e.g., puncture wounds). Animal bites, including human bites, expose the damaged tissue to a variety of pathogens that reflect the oral flora of the biting animal. Antibiotic management of wounds such as animal bites and puncture wounds is thus challenging, since the antibiotics used depend in large part on the potential pathogens that may have infected the wound. This can be especially problematic in individuals with antibiotic allergies, e.g., penicillin allergies, since treatment for these patients may require combination therapies to provide broad spectrum protection. In addition, certain animal bites, such as snake bites, also can result in severe inflammatory responses and/or tissue necrosis, which renders these bites especially prone to infection.

There is a need in the art for devices to promote healing and prevent infection in burns, bites, and other skin lesions that simultaneously provide a physical barrier and a chemical treatment for prevention of infection to aid the healing process. There is also a need for sterile methods of closure that can provide additional antibiotic protection to these wounds.

SUMMARY OF THE INVENTION

The present invention provides devices and compositions for the management of infection of topical wounds and lesions wherein the devices and compositions are given broad spectrum antibacterial properties by means of protonated/acidified nucleic acids. These modified nucleic acids may be present on the device surface, or integrated into the device or composition. Protonated/acidified nucleic acids have broad spectrum activity, i.e., are effective as bactericidal and/or bacteriostatic agents without regard to the class of bacteria, so are especially useful when identification of the infectious agent is difficult or when multiple infectious organisms are present. The nucleic acids used in the invention are protonated/acidified to give a pH when dissolved in water of less than pH 7 to about 1, more preferably less than pH 4.5 to about 1, and even more preferably less than pH 2 to about 1.

The nucleic acids of the invention may be protonated/acidified monomers or polymers. Polymers are preferably protonated/acidified oligonucleotides from 2-100 nucleotides in length. The nucleic acids of the invention may have nuclease resistant backbones, acid resistant backbones, and, in the preferred embodiment, have both acid resistant and nuclease resistant backbones.

In a first embodiment, the invention provides dressings for wounds which have protonated/acidified nucleic acids incorporated into or on the dressing to provide sterility and antibiotic activity. Such dressing may be comprised of any materials suitable for this use, e.g., polyester or acrylic mesh, and preferably, the dressings are a polyester mesh netting formed of woven multifilament polyester. Such dressing may also have a polymeric film bonded to one side of the coated solid substrate, preferably of about 0.001 inch+/−about 0.0005 inch.

In another embodiment, the invention provides sutures having a coating of an effective amount of protonated/acidified nucleic acids. The preferred sutures are nonabsorbable, multifilament sutures, preferably polyester sutures. The protonated/acidified nucleic acid on the suture is preferably from about 0.1 to about 5 percent of the dry weight of the suture. The amount used will be an "effective amount" meaning the amount needed to obtain the desired antibacterial effect over the period of time the dressing would be expected to be worn.

In yet another embodiment, the invention provides an adhesive composition having antibiotic properties for skin contact applications. The concentration of protonated/acidified nucleic acids in said polymer composition is about 0.1% to about 2% by weight. These adhesives contain an adhesive polymer with an effective amount of protonated/acidified nucleic acid dispersed throughout said polymer. The adhesive is preferably comprised of an acrylic polymer, and more preferably is a mixture of a low molecular weight solid acrylic polymer and a medium molecular weight solid acrylic polymer. In addition, the adhesive composition of the invention preferably has an effective amount of a tackifier.

In yet another embodiment, the invention provides wound sealants comprised of an effective amount of protonated/acidified nucleic acids, preferably about 0.1% to about 2% by weight. The wound sealant contains a fibrinogen activator in a concentration sufficient to initiate clot formation and may also contain fibrinogen and/or platelets. Preferably the fibrinogen activator is thrombin or batroxobin.

In yet another embodiment, the invention provides a skin substitute with an effective amount of protonated/acidified nucleic acids on its surface, or which has such modified nucleic acids impregnated into the skin substitute. The protonated/acidified nucleic acids in said skin substitute is preferably about 0.1% to about 2% by weight.

It is an object of the invention to provide a sterile environment for healing of wounds.

It is another object of the invention to provide methods of wound closure with additional antibiotic properties.

It is yet another object of the invention to prevent bacterial infection in burn victims.

It is another advantage of the invention that the mechanism of action of the protonated/acidified nucleic acids appears to be relatively non-specific, allowing them to be effective against any bacterium including clinically relevant pathogenic bacteria.

It is another advantage of the invention that the protonated/acidified nucleic acids are non-toxic to a subject treated with the modified nucleic acids.

It is a further advantage that the antibacterial effectiveness of protonated/acidified nucleic acids is neither length- nor sequence-dependent.

It is yet a further advantage that the protonated/acidified nucleic acids of the invention are economical to produce in large quantities, and thus are cost-effective for larger doses.

These and other objects, advantages, and features of the invention will become apparent to those persons skilled in the art upon reading the details of the antibiotic devices and formulations used in such devices as more fully described below.

BRIEF DESCRIPTION OF THE DRAWINGS

FIG. 1 is a graph illustrating the establishment of burn wound infection by subcutaneous and topical administration of *Psuedomonas aeruginosa*.

FIG. 2 is a graph illustrating the optimization of different routes of protonated/acidified oligonucleotide administration for treatment of burn wound infection.

DETAILED DESCRIPTION OF PREFERRED EMBODIMENTS

Before the present bandages are described, it is to be understood that this invention is not limited to particular materials or uses described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "nucleic acid" and "nucleic acid molecule" as used interchangeably herein, refer to a molecule comprised of nucleotides, i.e., ribonucleotides, deoxyribonucleotides, or both. The terms include monomers and polymers of ribonucleotides and deoxyribonucleotides, with the ribonucleotides and/or deoxyribonucleotides being connected together, in the case of the polymers, via 5' to 3' linkages. However, linkages may include any of the linkages known in the nucleic acid synthesis art including, for example, nucleic acids comprising 5' to 2' linkages. The nucleotides used in the nucleic acid molecule may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like.

The term "oligonucleotide" as used herein refers to a nucleic acid molecule comprising from about 2 to about 100 nucleotides, more preferably from 2 to 80 nucleotides, and even more preferably from about 4 to about 35 nucleotides.

The term "monomer" as used herein refers to a nucleic acid molecule and derivatives thereof comprised of a single nucleotide.

The terms "modified oligonucleotide", "modified monomer", and "modified nucleic acid molecule" as used herein refer to nucleic acids with one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. The internucleoside phosphate linkages can be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate and/or sulfone internucleotide linkages, or 3'-3', 2'-5', or 5'-5' linkages, and combinations of such similar linkages (to produce mixed backbone modified oligonucleotides). The modifications can be internal (single or repeated) or at the end(s) of the oligonucleotide molecule and can include additions to the molecule of the internucleoside phosphate linkages, such as cholesteryl, diamine compounds with varying numbers of carbon residues between amino groups and terminal ribose, deoxyribose and phosphate modifications which cleave or cross-link to the opposite chains or to associated enzymes or other proteins. Electrophilic groups such as ribose-dialdehyde could covalently link with an epsilon amino group of the lysyl-residue of such a protein. A nucleophilic group such as n-ethylmaleimide tethered to an oligomer could covalently attach to the 5' end of an mRNA or to another electrophilic site. The term modified oligonucleotides also includes oligonucleotides comprising modifications to the sugar moieties such as 2'-substituted ribonucleotides, or deoxyribonucleotide monomers, any of which are connected together via 5' to 3' linkages. Modified oligonucleotides may also be comprised of PNA or morpholino modified backbones where target specificity of the sequence is maintained.

The term "nucleic acid backbone" as used herein refers to the structure of the chemical moiety linking nucleotides in a molecule. This may include structures formed from any and all means of chemically linking nucleotides. A modified backbone as used herein includes modifications to the chemical linkage between nucleotides, as well as other modifications that may be used to enhance stability and affinity, such as modifications to the sugar structure. For example an α-anomer of deoxyribose may be used, where the base is inverted with respect to the natural β-anomer. In a preferred embodiment, the 2'-OH of the sugar group may be altered to 2'-O-alkyl or 2'-O-alkyl-n(O-alkyl), which provides resistance to degradation without comprising affinity.

The terms "acidification" and "protonation/acidification" as used interchangeably herein refer to the process by which protons (or positive hydrogen ions) are added to proton acceptor sites on a nucleic acid. The proton acceptor sites include the amine groups on the base structures of the nucleic acid and the phosphate of the phosphodiester linkages. As the pH is decreased, the number of these acceptor sites which are protonated increases, resulting in a more highly protonated/acidified nucleic acid.

The term "protonated/acidified nucleic acid" refers to a nucleic acid that, when dissolved in water at a concentration of approximately 16 $A_{260}$ per ml, has a pH lower than physiological pH, i.e., lower than approximately pH 7. Modified nucleic acids, nuclease-resistant nucleic acids, and antisense nucleic acids are meant to be encompassed by this definition. Generally, nucleic acids are protonated/acidified by adding protons to the reactive sites on a nucleic acid, although other modifications that will decrease the pH of the nucleic acid can also be used and are intended to be encompassed by this term.

The term "end-blocked" as used herein refers to a nucleic acid with a chemical modification at the molecular level that prevents the degradation of selected nucleotides, e.g., by nuclease action. This chemical modification is positioned such that it protects the integral portion of the nucleic acid, for example the coding region of an antisense oligonucleotide. An end block may be a 3' end block or a 5' end block. For example, a 3' end block may be at the 3'-most position of the molecule, or it may be internal to the 3' ends, provided it is 3' to the integral sequences of the nucleic acid.

The term "substantially nuclease resistant" refers to nucleic acids that are resistant to nuclease degradation, as compared to naturally occurring or unmodified nucleic acids. Modified nucleic acids of the invention are at least 1.25 times more resistant to nuclease degradation than their unmodified counterpart, more preferably at least 2 times more resistant, even more preferably at least 5 times more resistant, and most preferably at least 10 times more resistant than their unmodified counterpart. Such substantially nuclease resistant nucleic acids include, but are not limited to, nucleic acids with modified backbones such as phosphorothioates, methylphosphonates, ethylphosphotriesters, 2'-O-methylphosphorothioates, 2'-O-methyl-p-ethoxy ribonucleotides, 2'-O-alkyls, 2'-O-alkyl-n(O-alkyl), 2'-fluoros, 2'-deoxy-erythropentofuranosyls, 2'-O-methyl ribonucleosides, methyl carbamates, methyl carbonates, inverted bases (e.g., inverted T's), or chimeric versions of these backbones.

The term "substantially acid resistant" as used herein refers to nucleic acids that are resistant to acid degradation as compared to unmodified nucleic acids. Typically, the relative acid resistance of a nucleic acid will be measured by comparing the percent degradation of a resistant nucleic acid with the percent degradation of its unmodified counterpart (i.e., a corresponding nucleic acid with "normal" backbone, bases, and phosphodiester linkages). A nucleic acid that is acid resistant is preferably at least 1.5 times more resistant to acid degradation, or at least 2 times more resistant, even more preferably at least 5 times more resistant, and most preferably at least 10 times more resistant than its unmodified counterpart.

The term "$LD_{50}$" as used herein is the dose of an active substance that will result in 50 percent lethality in all treated experimental animals. Although this usually refers to invasive administration, such as oral, parenteral, and the like, it may also apply to toxicity using less invasive methods of administration, such as topical applications of the active substance.

The term "alkyl" as used herein refers to a branched or unbranched saturated hydrocarbon chain containing 1-6 carbon atoms, such as methyl, ethyl, propyl, tert-butyl, n-hexyl and the like.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing a bacterial disease from occurring in a subject who may be predisposed to the disease but has not yet been diagnosed as having it;

(b) inhibiting a bacterial disease, i.e., arresting its development; or (c) relieving a bacterial disease, i.e., causing regression and/or amelioration of the disease. The invention is directed toward treating patients with any infectious bacteria.

By the term "effective amount" or "therapeutically effective amount" of protonated/acidified nucleic acid is meant an amount of a protonated/acidified nucleic acid sufficient to obtain the desired physiological effect, e.g., suppression and/or prevention of bacterial infection. An effective amount of protonated/acidified nucleic acid is determined by the caregiver in each case on the basis of factors normally considered by one skilled in the art to determine appropriate dosages, including the age, sex, and weight of the subject to be treated, the condition being treated, and the severity of the wound or infection being treated.

Nucleic Acid Synthesis

Nucleic acids can be synthesized on commercially purchased DNA synthesizers from <1 uM to >1 mM scales using standard phosphoramidite chemistry and methods that are well known in the art, such as, for example, those disclosed in Stec et al., 1984, *J. Am. Chem. Soc.* 106:6077-6089, Stec et al., 1985, *J. Org. Chem.* 50(20):3908-3913, Stec et al., 1985, *J. Chromatog.* 326:263-280, LaPlanche et al., 1986, *Nuc. Acid. Res.* 14(22):9081-9093, and Fasman, 1989, *Practical Handbook of Biochemistry and Molecular Biology,* 1989, CRC Press, Boca Raton, Fla., herein incorporated by reference.

Nucleic acids can be purified by any method known to those in the art. In a preferred embodiment, they are purified by chromatography on commercially available reverse phase or ion exchange media, e.g., Waters Protein Pak, Pharmacia's Source Q, etc. Peak fractions can be combined and the samples desalted and concentrated by means of reverse phase chromatography on a poly(styrene-divinylbenzene) based media, such as Hamilton's PRP1 or PRP3, or Polymer Labs' PLRP resins. Alternatively, ethanol precipitation, diafiltration, or gel filtration may be used followed by lyophilization or solvent evaporation under vacuum in commercially available instrumentation such as Savant's SpeedVac. Optionally, small amounts of the nucleic acids may be electrophoretically purified using polyacrylamide gels.

Lyophilized or dried-down preparations of nucleic acids can be dissolved in pyrogen-free, sterile, physiological saline (i.e., 0.85% saline), sterile Sigma water, and filtered through a 0.45 micron Gelman filter (or a sterile 0.2 micron pyrogen-free filter). The described nucleic acids may be partially or fully substituted with any of a broad variety of chemical groups or linkages including, but not limited to: phosphoramidates; phosphorothioates; alkyl phosphonates; 2'-O-methyl; 2'-modified RNA; 2' methoxy ethoxy; morpholino groups; phosphate esters; propyne groups; or chimerics of any combination of the above groups or other linkages (or analogues thereof).

A variety of standard methods can be used to purify the presently described antibacterial nucleic acids. In brief, the antibacterial nucleic acids of the present invention can be purified by chromatography on commercially available reverse phase media (for example, see the RAININ Instrument Co., Inc. instruction manual for the DYNAMAX®-300A, Pure-DNA reverse phase columns, 1989, or current updates thereof, herein incorporated by reference) or ion exchange media such as Waters' Protein Pak or Pharmacia's Source Q (see generally Warren and Vella, 1994, "Analysis and Purification of Synthetic Nucleic Acids by High-Performance Liquid Chromatography", in *Methods in Molecular Biology,* vol. 26; *Protocols for Nucleic Acid Conjugates,* S. Agrawal, ed. Humana Press, Inc., Totowa, N.J.; Aharon et al., 1993, *J. Chrom.* 698:293-301; and Millipore Technical Bulletin, 1992, *Antisense DNA: Synthesis, Purification, and Analysis*). Peak fractions can be combined and the samples concentrated and desalted via alcohol (ethanol, butanol, isopropanol, and isomers and mixtures thereof, etc.) precipitation, reverse phase chromatography, diafiltration, or gel filtration.

A nucleic acid is considered pure when it has been isolated so as to be substantially free of, inter alia, incomplete nucleic acid products produced during the synthesis of the desired nucleic acid. Preferably, a purified nucleic acid will also be substantially free of contaminants which may hinder or otherwise mask the antibacterial activity of the oligonucleotide. A purified nucleic acid, after acidification by one of the disclosed methods or by any other method known to those of skill in the art, is a protonated/acidified nucleic acid that has been isolated so as to be substantially free of, inter alia, excess protonating/acidifying agent. In general, where a nucleic acid is able to bind to, or gain entry into, a target cell to modulate a physiological activity of interest, it shall be deemed as substantially free of contaminants that would render the nucleic acid less useful.

In particular embodiments, the nucleic acids of the invention are composed of one or more of the following: partially or fully substituted phosphorothioates, phosphonates, phosphate esters, phosphoroamidates, 2'-modified RNAs, 3'-modified RNAs, peptide nucleic acids, propynes or analogues thereof. The nucleic acids may be completely or partially derivatized by a chemical moiety including, but not limited to, phosphodiester linkages, phosphotriester linkages, phosphoramidate linkages, siloxane linkages, carbonate linkages, carboxymethylester linkages, acetamidate linkages, carbamate linkages, thioether linkages, bridged phosphoramidate linkages, bridged methylene phosphonate linkages, phosphorothioate linkages, methylphosphonate linkages, phosphorodithioate linkages, morpholino, bridged phosphorothioate linkages, sulfone internucleotide linkages, 3'-3' linkages, 5'-2' linkages, 5'-5' linkages, 2'-deoxy-erythropentofuranosyl, 2'-fluoro, 2'-O-alkyl nucleotides, 2'-O-alkyl-n(O-alkyl) phosphodiesters, morpholino linkages, p-ethoxy oligonucleotides, PNA linkages, p-isopropyl oligonucleotides, or phosphoramidates.

Protonated/Acidified Nucleic Acids

Subsequent to, or during, the above synthesis and purification steps, protonated/acidified forms of the described nucleic acids can be generated by subjecting the purified, or partially purified, or crude nucleic acids, to a low pH, or acidic, environment. Purified or crude nucleic acids can be protonated/acidified with acid, including, but not limited to, phosphoric acid, nitric acid, hydrochloric acid, acetic acid, etc. For example, acid may be combined with nucleic acids in solution, or alternatively, the nucleic acids may be dissolved in an acidic solution. Excess acid may be removed by chromatography or in some cases by drying the nucleic acid.

Other procedures to prepare protonated nucleic acids known to the skilled artisan are equally contemplated to be within the scope of the invention. Once the nucleic acids of the present invention have been protonated they may be separated from any undesired components like, for example, excess acid. The skilled artisan would know of many ways to separate the oligonucleotides from undesired components. For example, the oligonucleotide solution may be subjected to chromatography following protonation. In a preferred embodiment, the oligonucleotide solution is run over a poly (styrene-divinyl benzene) based resin (e.g., Hamilton's PRP-1 or PRP-3 and Polymer Lab's PLRP) following protonation.

The protonated/acidified nucleic acids can be used directly, or in a preferred embodiment, processed further to remove any excess acid and salt via precipitation, reverse phase chromatography, diafiltration, or gel filtration. The protonated/acidified oligos can be concentrated by precipitation, lyophilization, solvent evaporation, etc. When suspended in water or saline, the acidified nucleic acid preparations of the invention typically exhibit a pH of between 1 and 4.5 depending upon the level of protonation/acidification, which can be determined by how much acid is used in the acidification process. Alternatively, nucleic acids can be protonated by passage over a cation exchange column charged with hydrogen ions.

Acid and Nuclease Resistant Nucleic Acids

Generally, nucleic acid preparations near pH 2 to 1 demonstrate better antibacterial activity than nucleic acids at or near pH 4.5. Many oligo backbones are not stable at pH 2 and experience depurination, although a number of backbones are relatively stable at a pH of 4 to 5. It has been discovered that 2'-O-alkyl, 3'-O-alkyl, and 2'-O-alkyl-n(O-alkyl) nucleic acids are stable at the desired pH of 2 to 1.

In one embodiment, the invention uses nucleic acids that are substantially nuclease resistant. This includes nucleic acids completely derivatized by phosphorothioate linkages, 2'-O-methylphosphodiesters, 2'-O-alkyl, 2'-O-alkyl-n(O-alkyl), 2'-fluoro, 2'-deoxy-erythropentofuranosyl, p-ethoxy, morpholino nucleic acids, p-isopropyl nucleic acids, phosphoramidates, chimeric linkages, and any other backbone modifications, as well as other modifications, which render the nucleic acids substantially resistant to endogenous nuclease activity. Additional methods of rendering nucleic acids nuclease resistant include, but are not limited to, covalently modifying the purine or pyrimidine bases that comprise the nucleic acid. For example, bases may be methylated, hydroxymethylated, or otherwise substituted (e.g., glycosylated) such that the nucleic acids comprising the modified bases are rendered substantially nuclease resistant.

Although 2'-O-alkyl substituted nucleic acids and molecules with similar modifications exhibit marked acid stability and endonuclease resistance, they are sensitive to 3' exonucleases. In order to enhance the exonuclease resistance of 2'-O-alkyl substituted nucleic acids, the 5' and 3' ends of the ribonucleic acid sequence are preferably attached to an exonuclease blocking function. For example, one or more phosphorothioate nucleotides can be placed at either end of the oligoribonucleotide. Additionally, one or more inverted bases can be placed on either end of the oligoribonucleotide, or one or more alkyl, e.g., butanol-substituted nucleotides or chemical groups can be placed on one or more ends of the oligoribonucleotide. An enzyme-resistant butanol preferably has the structure $CH_2CH_2CH_2CH_2$—OH (4-hydroxybutyl) which is also referred to as a C4 spacer. Accordingly, a preferred embodiment of the present invention is a protonated/acidified nucleic acid comprising an antibacterial nucleic acid having the following structure:

A-B-C wherein "B" is a 2'-O-alkyl or 2'-O-alkyl-n(O-alkyl) oligoribonucleotide between about 1 and about 98 bases in length, and "A" and "C" are respective 5' and 3' end blocking groups (e.g., one or more phosphorothioate nucleotides (but typically fewer than six), inverted base linkages, or alkyl, alkenyl, or alkynl groups or substituted nucleotides). A partial list of blocking groups includes inverted bases, dideoxynucleotides, methylphosphates, alkyl groups, aryl groups, cordycepin, cytosine arabanoside, 2'-methoxy-ethoxy nucleotides, phosphoramidates, a peptide linkage, dinitrophenyl group, 2'- or 3'-O-methyl bases with phosphorothioate linkages, 3'-O-methyl bases, fluorescein, cholesterol, biotin, acridine, rhodamine, psoralen and glyceryl.

Wound Treatment

The devices of the invention can be used in the management and care of any of a variety of wounds and lesions, including but not limited to abrasions, burns, lacerations, puncture wounds, bites, chronic fungating lesions, chronic pressure ulcers, traumatic wounds and the like. The devices of the invention are useful in the closure and protection of these wounds, and to help promote wound management and the healing process. The particular device of the invention to be used for any given wound will depend on the nature and extent of the wound, as will be apparent to one skilled in the art upon reading the present disclosure.

Wound Dressings

The first embodiment of the invention provides a dressing comprised of a flexible solid substrate and protonated/acidified nucleic acids intended for use as a temporary dressing on burns, wounds and other lesions. The dressing forms a barrier against bacterial or other contamination. The dressing preferably remains flexible and facilitates movement, promoting early physical therapy. The nucleic acid formulations may be impregnated into the dressing, or may be a coating on the dressing, with the coating on the side to lie adjacent to the patient. Types of wound care dressings encompassed by the invention include, but are not limited to, alginates, composits, exudate absorbers, foams, gauzes, hydrocolloids, and hydrogels. Exemplary bandages for use with the present invention include, but are not limited to, those described in U.S. Pat. Nos. 5,718,674, 5,692,937, 5,499,966, 5,376,067, 4,867,821, 4,672,956, 4,655,202 and 4,377,159.

The dressing of the invention may be formed from any material known in the art, including biologically derived materials and synthetic materials. Preferably, the flexible solid substrate is a synthetic material, and more preferably a woven synthetic material in the form of a mesh. In a preferred embodiment, the flexible substrate is a multifilament or monofilament polyester mesh sheet. In another example, a sponge or other substrate may replace the mesh netting, where medically appropriate and if its properties match the desired end. The protonated/acidified nucleic acids are applied to the substrate of the dressing, e.g., a fibrous mesh netting, as an aqueous solution and dehydrated.

The dressing may be used directly, or may be adhered to a backing, e.g., a self-adhesive backing. Such backing is preferably of a flexible material, and even more preferably has an adhesive on the backing surrounding the dressing to allow self-adhesion of the bandage. In one example, the backing is a flexible strip having a coating of adhesive deposited on at least the lower planar surface of the strip. A dressing pad of the invention is attached to the lower planar surface of the strip and centered such that a portion of the adhesive strip extends from each end of the wound pad. The wound pad and strip are die cut in a predetermined shape, thereby separating the wound pad and strip into an outer surrounding frame and inner bandage. Such bandages are described in U.S. Pat. Nos. 5,792,092 and 5,685,833, which are incorporated herein by reference.

The dressing of the invention can also be separate and held in place by the elastic forces of a bandage, e.g., a gauze coated with protonated/acidified nucleic acids held in place by an elastic bandage. Elastic bandages for use in the invention preferably have good elastic properties which can be uniform over the width of the bandage. The fabric may be woven or preferably non-woven. The use of a non-woven fabric in elastic bandages of the invention can provide a desirable textile 'feel' to the surface of the bandage. Additionally use of an absorbent non-woven fabric can provide the bandage with a degree of absorbency for water and body fluids such as blood. In one example, an elastic bandage can be used which comprises an inner layer of fabric and an outer layer of fabric bonded to a central layer, such as is described in U.S. Pat. No. 4,414,970.

A vapor permeable film of plastic material occlusive to moisture and bacteria may additionally be joined to one side of the impregnated mesh netting to form an external surface of the dressing. The cast dressing is then cut to the desired size of individual dressings.

The protonated/acidified nucleic acids of the invention may be added in an amount that allows effective dissemination of the biocidal activity from the adhesive preparation.

Sutures

Sutures are often used in the closing of a wound, and currently suturing is the method of choice for closing most surgical wounds. The type of suture used will vary depending on the type and extent of the wound, the tissue involved, and a particular patient's healing ability.

Sutures within the scope of this invention can be of any type used or contemplated for use in wound closure. The suture can be synthetic or natural, absorbable or nonabsorbable, or a monofilament or multifilament in a braided, twisted or covered form. In addition, the sutures can be attached to one or more needles, if desired. Examples of absorbable monofilament sutures include natural sutures such as surgical gut and collagen, and synthetic sutures such as homopolymers and copolymers of p-dioxanone. Examples of absorbable multifilament sutures include sutures prepared from fiber-forming polymers of one or more lactones, e.g., Vicryl.®. poly(lactide-co-glycolide) multifilament suture. Examples of nonabsorbable monofilament and multifilament sutures include nylon, polypropylene, steel, polyvinylidene fluoride, linen, cotton, silk, and polyesters such as polyethylene terephthalate (PET). The preferred sutures are nonabsorbable, multifilament sutures, preferably polyester sutures. The most preferred suture is PET.

The protonated/acidified nucleic acids of the invention may be added in an amount that allows effective biocidal activity from the coating. Generally, the protonated/acidified nucleic acid is used in a concentration of 0.5 to 40%, more preferably 1.0 to 20%, even more preferably between 5% to 10%.

Adhesives

The present invention includes an adhesive compound which incorporates an adhesive component containing a protonated/acidified nucleic acid preparation. The protonated/acidified nucleic acids are preferably homogeneously dispersed throughout the adhesive layer. Active protonated/acidified nucleic acids of the present composition disassociate from the surface or leach out of the adhesive matrix over time, delivering biocidal activity at a distance from the adhesive surface.

The adhesive of the present invention is specifically suited for use in skin contact applications during and after medical procedures, for example, as an adhesive in surgical drapes, wound dressings and tapes. The preferred adhesive composition incorporates acrylic polymers and added tackifiers to form an adhesive which is particularly suited for use in medical procedures.

A preferred combination of acrylic polymers to form the adhesive composition includes the combination of a low molecular weight solid acrylic polymer and a medium molecular weight solid acrylic polymer in a ratio of about 1 to 4, respectively, to optimize the adhesion of the adhesive to skin, cohesion and resistance to cold flow. A low molecular acrylic polymer is a polymer having a molecular weight ranging from about 90,000 to about 120,000, while a medium molecular weight acrylic polymer has a molecular weight ranging from about 140,000 to about 160,000. Suitable low molecular weight solid acrylic polymers and medium molecular weight solid acrylic polymers are available from Schenectady International, Inc. under Product Nos. HRJ-4326 and HRJ-10127, respectively.

The adhesive component of the composition can also include tackifiers as are well known in the art. Tackifiers contemplated include SYLVATEC, ZONAREZ and FORAL which are available from Arizona Chemical and Hercules, Inc.

The protonated/acidified nucleic acids of the invention may be added in an amount that allows effective dissemination of the biocidal activity from the adhesive preparation. Generally, the protonated/acidified nucleic acid is used in a concentration of 0.5 to 40%, more preferably 1.0 to 20%, even more preferably between 5 to 10%.

Wound Sealant

In yet another embodiment of the invention, a wound sealant comprising protonated/acidified nucleic acids are used to aid in wound closure. Wound sealants can be used alone or with additional help from other closing devices or methods. For example, wound sealants can be used in conjunction with sutures, adhesive tape, bandages, and the like to improve wound closure integrity. Wound sealant can also be used alone in situations involving coagulopathy, friable tissues, adhesions that cause bleeding when sutures would be ineffective to control the bleeding, and the like. Other potential uses of wound sealants of the invention include sealing vascular suture lines, reinforcing pulmonary and esophageal staple lines and fixing split-thickness skin grafts. See Spotnitz et al., *Wound Healing,* 77:651-669 (1997).

One example of a wound sealant is fibrin sealant, which is comprised of fibrinogen and a fibrinogen activator such as thrombin and batroxobin. The fibrinogen activator can be present in various concentrations depending on the desired time to form a clot. When the fibrinogen activator is thrombin, at thrombin concentrations greater than 100 units per ml or so in the wound sealant, the fibrinogen concentration becomes the rate limiting step in coagulation. At concentrations lower than about 100 μ/ml, the thrombin level is the rate controlling substance in the wound sealant. Thus, thrombin concentration can be used to control the time to gelation.

Another example of a wound sealant is a platelet glue wound sealant comprising a plasma-buffy coat concentrate as described in U.S. Pat. No. 5,733,545. This sealant contains platelets, fibrinogen, and a fibrinogen activator in a concentration sufficient to initiate clot formation.

The protonated/acidified nucleic acids of the invention may be added in an amount to effectively treat and/or prevent infection in situs of a wound. Generally, the protonated/acidified nucleic acid is used in a concentration of 0.5 to 40%, more preferably 1.0 to 20%, even more preferably between 5 to 10%.

Skin Substitutes

Another embodiment of the invention provides skin substitutes comprising protonated/acidified nucleic acids. Skin substitutes are commonly used as dressings, especially for burn victims. They can be used to maintain a clean wound environment until skin grafting can be achieved, or may be a dressing placed on a partial-thickness wound. In another embodiment of the invention, substitute skin dressings are provided with protonated/acidified nucleic acids either coated on the surface to be placed adjacent to the patient, or interspersed throughout the skin substitute. For a review of such skin substitutes, see Staley et al., *Adv. Wound Care* 10:39-44 (1997).

Biological dressings that may be used in the invention fall into three categories: heterografts or xenografts (e.g., pig skin), homografts or allografts (e.g., cadaver skin) and amnion (placenta). These dressings may be coated on the surface intended to contact the patient with an effective amount of the modified nucleic acids of the invention.

Preferably, the skin substitutes of the invention are biosynthetic dressings. These include: Biobrane, a flexible nylon fabric impregnated with collagen and bonded to a silicone membrane; collagen derivatives such as SkinTemp, Medifil, Kollagen, which are typically formed from animal collagen; EZ-Derm, a pigskin impregnated with the preservative aldehyde; and Alginates, which are derived from seaweed and release calcium ions to help with homeostasis. These dressings may be coated with the protonated/acidified nucleic acids of the invention and/or have the modified nucleic acids impregnated into the fiber of the dressing.

Cultured skin substitutes may also be used in the present invention. These include: cultured epidermal autografts, which are produced from a patient's own keratinocytes; Dermagraft, having a collagen base with human neonatal fibroblasts injected into the matrix; Composite skin, Graft skin, a bilayered cultured skin containing human fibroblasts on a bovine collagen lattice; Alloderm, an allograft dermis with all immune cells removed; and Integra, a bovine collagen dermis with an outer silicone membrane layer.

Other similar skin substitutes can also be used, as will be apparent to one skilled in the art upon reading this disclosure.

The skin substitute may be impregnated with the protonated/acidified oligonucleotide, or it may be coated on the side that will contact the patient. The solution used for impregnation or coating may be in any concentration, but is preferably 0.1 to 40% nucleic acid, more preferably 1.0 to 20%, even more preferably between 5 to 10%.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Protonation/Acidification of Nucleic Acids

Protonated/acidified forms of the described nucleic acids can be generated by subjecting purified, partially purified, or crude nucleic acids, to a low pH (e.g., acidic) environment. Purified or crude nucleic acids were protonated/acidified with acid chosen from a group including phosphoric acid, nitric acid, hydrochloric acid, and acetic acid.

Pooled fractions of a strong anion exchange (SAX)-purified oligonucleotide (at approximately 2-25 $A_{260}$ per ml) were pumped onto a PRP (Hamilton Co.) column. This was followed immediately with an excess of dilute acid (e.g., 25 mM HCl) until the eluent was acidic. The column was then washed with purified water (no salt or buffers) until the conductivity and pH of the eluent returned to essentially background levels. The oligonucleotide was then dried down in a commercially available vacuum evaporator. Alternatively, the oligonucleotide was suspended in dilute acid and either chromatographed over the PRP or similar column as described above, or chromatographed over a size exclusion column (e.g., BioRad Biogel P2 or P4) using water as solvent. Alternatively, a desalted nucleic acid may be dissolved in alkaline salt solution (e.g., 0.4 M NaCl and pH 12, 25 mM NaOH), run on a PRP column, washed with acid followed by water, and then eluted, as described above. Alternatively, a nucleic acid may be chromatographed over a cation exchange column that is in the H+ form, collected and dried down as described above.

Nucleic acids were also acidified by adding an acid, e.g., HCl (0.1 N), directly to a nucleic acid solution (approximately 300 $A_{260}$ per ml) until the pH of the solution reached pH 1 to pH 3. The acidified nucleic acids can then be run over an acid stable size exclusion column such as a BioRad Biogel P2 or P4 column.

Lyophilized or dried-down preparations of nucleic acids to be used in bacterial experiments were dissolved in pyrogen-free, sterile, physiological saline (i.e., 0.85% saline), sterile Sigma water, and filtered through a 0.45 micron Gelman filter (or a sterile 0.2 micron pyrogen-free filter prior to animal studies).

When suspended in water or saline, the nucleic acid preparations typically exhibited a pH between 1 and 4.5 depending upon the level of protonation/acidification, which is determined by how much acid is used in the acidification process.

Example 2

Bacterial Growth Studies

The efficacy of the protonated/acidified nucleic acids of the invention is shown in the following bacterial growth studies.

Limited Nutrient Growth Study

For the limited nutrient growth study, cells were taken off plates and suspended in PBS to give a final concentration of $10^5$ CFU/ml and a final volume of 1 ml. Mueller-Hinton broth was added (40 µl for *S. aureus* ACC # 13301, 20 µl for *P. aeruginosa* ACC # 10145). 100 µl of water or 100 µl of nucleic acid (32 $A_{260}$ units, 2'-O-methyl ribonucleotides, phosphodiester linkage, 5' and 3' inverted T end-blocked, sequence CGCCATTGG, SEQ ID NO: 1) was added and the tubes were incubated at 35° C. without shaking for approximately 24 hours. The $A_{625}$ was measured and the percent inhibition calculated as a percent of the control. The results are in the following table:

| Bacteria | pH of Nucleic Acid | Inhibition of Growth (%) |
| --- | --- | --- |
| S. aureus | Water Control-pH 7 | 0 |
| S. aureus | 2 | 100 |
| S. aureus | 3 | 100 |
| S. aureus | 4 | 100 |
| S. aureus | 5 | 16 |
| S. aureus | 7 | 0 |
| P. aeruginosa | Water Control-pH 7 | 0 |
| P. aeruginosa | 2 | 100 |
| P. aeruginosa | 3 | 100 |
| P. aeruginosa | 4 | 100 |
| P. aeruginosa | 5 | 0 |
| P. aeruginosa | 7 | 0 |

Stationary Growth Study

A stationary growth assay was also performed to study the effect of pH on the anti-bacterial activity of nucleic acids. Cells were taken off plates and suspended in saline to give a final concentration of $10^7$ CFU/ml of *S. aureus* in 1 ml of PBS. 100 μl of water or 100 μl of nucleic acid (32 $A_{260}$ units, 2'-O-methyl ribonucleotides, phosphodiester linkage, 5' and 3' inverted T end blocked, sequence CGCCATTGG, SEQ ID NO: 1) was added and the tubes were incubated at 35° C. without shaking for approximately 24 hours. Aliquots were plated directly or after dilutions and incubated at 37° C. and colonies counted after 24 hours. The results are in the following table:

| Bacteria | pH of Nucleic Acid | CFU/ml |
|---|---|---|
| *S. aureus* | Water Control-pH 7 | $10^7$ |
| *S. aureus* | 2 | 0 |
| *S. aureus* | 3 | $10^3$ |
| *S. aureus* | 4 | $10^6$ |
| *S. aureus* | 5 | $10^7$ |
| *S. aureus* | 7 | $10^7$ |

From these results, it was concluded that lowering the pH of a nucleotide conferred upon it bactericidal and bacteriostatic effects. Next, the effect of sequence identity and length were explored.

Example 3

Sequence Effects on Antibacterial Activity

First, a stationary growth assay was performed to study the effect of sequence length. Cells were taken off plates and suspended in saline to give a final concentration of $10^7$ CFU/ml of Strep. mutans in 1 ml of PBS. 50 μl of water or 50 μl of nucleic acids of varying length (16 $A_{260}$ units) were added and the tubes incubated at 35° C. without shaking for approximately 24 hours. Each of the nucleic acids used consisted of 2'-O-methyl substituted ribonucleotides phosphodiester linked with 5' and 3' inverted T end-blocking. The sequences were: 114.6-CGCCAT (SEQ ID NO: 2); 114.12-ACGCGCCATTGG (SEQ ID NO: 3); 114.21-GGAACGCGCCATTGGTATATC (SEQ ID NO: 4). The lengths reported in the following table for each nucleic acid include the inverted T's at the 5' and 3' ends. Aliquots were plated directly or after dilutions and incubated at 37° C. and colonies counted after 24 hours. The results are in the following table:

| Bacteria | Nucleic Acid | Length (Bases) | pH | Inhibition (%) | CFU/ml |
|---|---|---|---|---|---|
| *Strep. mutans* | Water Control | 0 | 7 | 0 | $10^7$ |
| *Strep. mutans* | 114.6 | 8 | 3 | 100 | 0 |
| *Strep. mutans* | 114.12 | 14 | 3 | 100 | 0 |
| *Strep. mutans* | 114.21 | 23 | 3 | 100 | 0 |
| *Strep. mutans* | 114.6 | 8 | 7 | 0 | $10^7$ |
| *Strep. mutans* | 114.12 | 14 | 7 | 0 | $10^7$ |
| *Strep. mutans* | 114.21 | 23 | 7 | 0 | $10^7$ |

Next, a limited nutrient growth assay was performed to study the effects of nucleotide homopolymers (AAAAAAAAAAAA, SEQ ID NO: 5; UUUUUUUUUUUU, SEQ ID NO: 6; GGGGGGGGGGGG, SEQ ID NO: 7; CCCCCCCCCCCC, SEQ ID NO: 8). Each homopolymer used consisted of 2'-O-methyl substituted ribonucleotides phosphodiester linked, with both 3' and 5' butanol end-blocking. Cells were taken off plates and suspended to give a final concentration of $10^5$ CFU/ml in 1 ml of PBS. Mueller-Hinton broth was added (40 μl for *S. aureus* ACC # 13301, 20 μl for *P. aeruginosa* ACC # 10145). 100 μl of water or 100 μl of nucleic acid at pH 1.5 (32 $A_{260}$ units) were added and the tubes were incubated at 35° C. without shaking for approximately 24 hours. The $A_{625}$ was measured and the percent inhibition calculated as a percent of the control. The results are in the following table:

| Bacteria | Oligonucleotide, pH 1.5 | Inhibition (%) |
|---|---|---|
| *S. aureus* | Water Control - pH 7 | 0 |
| *S. aureus* | Homopolymer, 12 A | 100 |
| *S. aureus* | Homopolymer, 12 C | 100 |
| *S. aureus* | Homopolymer, 12 G | 100 |
| *S. aureus* | Homopolymer, 12 U | 100 |
| *P. aeruginosa* | Water Control - pH 7 | 0 |
| *P. aeruginosa* | Homopolymer, 12 A | 100 |
| *P. aeruginosa* | Homopolymer, 12 C | 100 |
| *P. aeruginosa* | Homopolymer, 12 G | 100 |
| *P. aeruginosa* | Homopolymer, 12 U | 100 |

Next, a limited nutrient growth assay was performed to study the effects of monomers, dimers and trimers. Each nucleic acid used consisted of 2'-O-methyl substituted ribonucleotides phosphodiester linked, with both 3' and 5' blocking with butanol. The nucleic acid designated 114.12 had a sequence of ACGCGCCATTAT, SEQ ID NO: 9. Cells were taken off plates and suspended to give a final concentration of $10^5$ CFU/ml in 1 ml of PBS. Mueller-Hinton broth was added (40 μl for *S. aureus* ACC # 13301, 20 μl for *E. coli* ACC # 35218). 25 μl of water or 25 μl of nucleic acid at pH 1.5 (8 $A_{260}$ units) were added and the tubes were incubated at 35° C. without shaking for approximately 24 hours. The $A_{625}$ was measured and the percent inhibition calculated as a percent of the control. Aliquots were plated directly or after dilutions and incubated at 37° C. and colonies counted after 24 hours to determine CFUs. The results are in the following table:

| Bacteria | Nucleic Acid | Length (Bases) | Inhibition (%) | CFU/ml |
|---|---|---|---|---|
| *S. aureus* | Water Control | 0 | 0 | $10^6$ |
| *S. aureus* | G | 1 | 100 | $10^3$ |
| *S. aureus* | U | 1 | 100 | $10^2$ |
| *S. aureus* | GU | 2 | 100 | $10^3$ |
| *S. aureus* | AUG | 3 | 100 | $10^3$ |
| *S. aureus* | 114.12 | 12 | 100 | $10^3$ |
| *E. coli* | Water Control | 0 | 0 | $10^8$ |
| *E. coli* | G | 1 | 100 | $10^3$ |
| *E. coli* | U | 1 | 100 | $10^2$ |
| *E. coli* | GU | 2 | 100 | $10^3$ |
| *E. coli* | AUG | 3 | 100 | $10^4$ |
| *E. coli* | 114.12 | 12 | 100 | $10^3$ |

A stationary phase assay was performed to study the effects of monomers, dimers and trimers. Each nucleic acid used consisted of 2'-O-methyl substituted ribonucleotides phosphodiester linked, with both 3' and 5' blocking with butanol. The nucleic acid designated 114.12 had a sequence of ACGCGCCATTAT, SEQ ID NO: 9. Cells were taken off plates and suspended in saline to give an $A_{625}$ of 0.08 for *S. aureus*, 0.12 for *E. coli*, and 0.1 for *K. pneumoniae* in 1 ml of PBS. 25 μl of water or 25 μl of nucleic acid (8 $A_{260}$ units) were added and the tubes incubated at 35° C. without shaking for approximately 24 hours. Aliquots were plated directly or after dilutions and incubated at 37° C. and colonies counted after 24 hours to determine CFUs. The results are in the following table:

| Bacteria | Nucleic Acid | Length (Bases) | CFU/ml |
|---|---|---|---|
| S. aureus | Water Control | 0 | $10^6$ |
| S. aureus | G | 1 | 0 |
| S. aureus | U | 1 | 0 |
| S. aureus | GU | 2 | 0 |
| S. aureus | AUG | 3 | 0 |
| S. aureus | 114.12 | 12 | 0 |
| E. coli | Water Control | 0 | $10^7$ |
| E. coli | G | 1 | 0 |
| E. coli | U | 1 | 0 |
| E. coli | GU | 2 | 0 |
| E. coli | AUG | 3 | 0 |
| E. coli | 114.12 | 12 | 0 |
| K. pneumoniae | Water Control | 0 | $10^8$ |
| K. pneumoniae | G | 1 | $10^2$ |
| K. pneumoniae | U | 1 | $10^1$ |
| K. pneumoniae | GU | 2 | $10^1$ |
| K. pneumoniae | AUG | 3 | $10^1$ |
| K. pneumoniae | 114.12 | 12 | $10^2$ |

In conclusion, these results demonstrate that the ability of protonated/acidified nucleic acids to function as an antibacterial agent is independent of sequence identity. Furthermore, homopolymers and nucleic acids as short as monomers are also effective. These results indicate that although sequence may play a role in the activity of the oligonucleotide, there is also another mechanism of the anti-bacterial effect which is not antisense dependent, and is thus sequence independent.

Example 4

Protonated/Acidified Nucleic Acid Efficacy in a Topical *Pseudomonas* Burn Model of Infection Protonated/acidified nucleic acids were evaluated for their in vivo therapeutic efficacy for the treatment of burn wound infection caused by *Pseudomonas aeruginosa*. A burn wound infection model was established in mice using a highly pathogenic burn wound clinical isolate of *P. aeruginosa*. Lethality doses of the bacteria were determined for two routes of infection (subcutaneous and topical), representing systemic and local forms of infection.

Animals

Six week old BALB/c female mice were obtained from the mouse breeding colony at DRES, with breeding pairs purchased from Charles River Canada Ltd. (St. Constant, Quebec, Canada). The use of animals described in this study was approved by DRES Animal Care Committee. Care and handling of animals described in this study followed guidelines set out by the Canadian Council on Animal Care.

Using this infection model, treatment with protonated/acidified nucleic acids using various routes of drug administration was evaluated and optimized. The protonated/acidified nucleic acids tested are summarized in the following table:

| Protonated/acidified Nucleic Acids | Chemical Structure |
|---|---|
| B2 | HO—$CH_2CH_2CH_2CH_2$-ACg•CgC•CAU•Ugg-$CH_2CH_2CH_2CH_2$—OH pH (1.5-2.0) |
| B7 | HO—$CH_2CH_2CH_2CH_2$-ACg•CgC•CAU•Ugg-$CH_2CH_2CH_2CH_2$—OH pH(~4.5) |
| BUB | dihydroxydibutyldiphophate 2'-O-methyl uridine pH (1.5-2.0) |
| C2 | dibutyl-diphosphate 2'-O-methyl uridine |
| 2 | HO—$CH_2CH_2CH_2CH_2$-AUG-$CH_2CH_2CH_2CH_2$—OH |
| 3 | HO—$CH_2CH_2CH_2CH_2$-G-$CH_2CH_2CH_2CH_2$—OH |
| 4 | HO—$CH_2CH_2CH_2CH_2$—UUU—$CH_2CH_2CH_2CH_2$—OH |
| 5 | HO—$CH_2CH_2CH_2CH_2$-GGG-$CH_2CH_2CH_2CH_2$—OH |
| 6 | 2'-O-methyl Uridine monophosphate |
| 7 | HO—$CH_2CH_2CH_2CH_2$-CgC•CAU—$CH_2CH_2CH_2CH_2$—OH |

Bacteria

*Pseudomonas aeruginosa* (Strain Utah 4) was initially cultured on the tripticase soya broth, aliquoted, and frozen at 70° C. Prior to use, aliquots were thawed and diluted serially in sterile PBS just prior to administration into animals. To ensure viability and virulence, aliquots of the bacteria were periodically re-amplified in tripticase soya broth and colonies determined on tripticase soya agar plates.

Establishment of Burn Wound Infection

Burn wound infection in mice can be established by subcutaneous or topical administration of the bacteria to the sites of the burn. $LD_{50}$ values were determined using the method of Reed and Muench, and were found to be approximately $4 \times 10^8$ and $2 \times 10^9$ CFUs, respectively, for subcutaneous and topical routes of infection. These lethal dosages of the *P. aeruginosa* strain used were found to change during the course of this study due to possible decreases in bacterial viability and virulence during storage. As a result, these values were regularly re-checked and adjusted. For all treatment studies, approximately 5 $LD_{50}$ of the bacteria were used. The survival pattern of the mice infected with 5 $LD_{50}$ of the bacteria administered by these two routes of infection was similar (FIG. 1). Both routes of administration resulted in eventual death of all mice in the test groups by day 3 post infection. All control animals which received equivalent doses of bacteria by either subcutaneous or topical administration without the burn were asymptomatic and found to be completely resistant to the infection, In the mice that received the burn and infection, the $LD_{50}$ of the bacteria administered topically was approximately 5-fold higher than the subcutaneous route. Unless otherwise stated, all treatment studies described below were carried out using the subcutaneous route of infection. This route of administration was chosen for subsequent studies as it does not require pretreatment of the mice with cyclophosphamide at three days prior to infection, and it causes a stronger systemic infection.

For establishing the lethal doses of the bacteria for the systemic burn wound infection, groups of mice were anesthetized with ketamine/xylazine mixture (50 mg/kg each, given intramuscularly), their backs were then shaved using a clipper, razor and shaving cream. To induce a burn in the back of these animals, a brass bar (10×10×100 mm) was heated in boiling water for 15 minutes. The end of the heated bar was then applied on the shaved back of the mice for 45 seconds. After a waiting period of 30 minutes, 50 µl of the bacterial inoculum (containing approx. $1 \times 10^{8-11}$ CFU of total bacteria) was then applied subcutaneously into the sites of the burn on the animal back. The mice were then allowed to recover and were monitored daily for symptoms and deaths. For establishment of a topical infection, the mice were pre-primed with cyclophosphamide (200 mg/kg body weight, i.p.). Three days later, the mice were shaved and burns were induced as described above. The inoculum, containing the same numbers of bacteria, was then topically applied (100 µl) evenly on the sites of the burn, and a custom made "mouse jacket" was then put on the infection site, for at least 2 hours. These mice were then monitored daily for symptoms and deaths.

Treatment of Burn Wound Infection

To determine the effectiveness of various protonated/acidified nucleic acids for the treatment of burn wound infection, mice were subcutaneously or topically infected with 5 $LD_{50}$ of *P. aeruginosa* as described above. Mice were then treated in the following manner. For treatment of systemic infection (infection by subcutaneous injection of the bacteria), mice were treated at 2 and 8 hours post infection on day 1, and twice daily on days 2 and 3. Treatment with various protonated/acidified nucleic acids was administered subcutaneously, intravenously and/or topically. For topical treatment of burn wound infection, mice were treated on the same schedule as on intravenous/subcutaneous treatment. The concentrations of the protonated/acidified nucleic acids were 335-360 A/ml for subcutaneous (volume 200 µl) and intravenous (volume 100 µl) administrations, 1800 A/ml for topical administration (50 µl).

Bacterial Determination of Organ Homogenates

To determine the bacterial load in the blood and organs of experimental animals, blood, spleens, livers and the burnt skins were aseptically removed. The blood (100 µl) was serially diluted in sterile PBS and 100 µl of the diluted blood was plated for growth in tripticase soya agar plates. For the organs, they were homogenized in 2 ml (spleens and skins) or 5 ml (livers) of sterile PBS using a hand-held tissue grinder. The tissue homogenates were serially diluted in sterile PBS, plated for growth in TSA, and the inoculated plates were incubated at 37° C. overnight. The number of CFUs was then determined by the presence of colonies on these plates.

Statistics

The survival rates of control and treated mice were compared using the Mann-Whitney impaired nonparametric one-tailed test. These tests were performed using the GraphPad Prism software program (version 2.0; GraphPAD Software, Inc., San Diego, Calif.). Differences were considered statistically significant at $p<0.05$.

Optimization of Routes of Administration

To determine the most effective route(s) of administration for the oligonucleotides, mice which were systemically infected were treated with protonated/acidified B2 by the subcutaneous and intravenous routes (FIG. 2). Using both subcutaneous and intravenous routes to treat mice was found to be the most efficacious, resulting in 100% survival rate ($p<0.01$ vs control). When treatment was administered by subcutaneous or intravenous route alone, the efficacies were 40% ($p>0.05$ vs control) and 80% ($p<0.05$ vs. control), respectively. These results indicate that using both subcutaneous and intravenous administrations of the protonated/acidified nucleic acids provides optimal therapeutic effectiveness against systemic burn wound infection.

A total of 12 protonated/acidified oligonucleotides were tested and of these, two, B2 and U, were found to be extremely efficacious in the post exposure treatment of burn wound infection (90-100% survival rates vs. 0% for untreated control, $p<0.01$). The comparative efficacy of these protonated/acidified nucleic acids in all studies is summarized below in the following table:

| Protonated/acidified Nucleic Acids | # Survivors/Total Animals Tested | % Survival | p < Infected Control |
|---|---|---|---|
| No Treatment Control | 1/45 | 2 | — |
| B2 | 28/30 | 93 | <0.0001 |
| B7 | 2/5 | 40 | 0.0867 |
| BUB | 7/8 | 87.5 | <0.0001 |
| C2 | 17/18 | 94 | <0.0001 |
| 2 | 3/5 | 60 | 0.0184 |
| 3 | 3/5 | 60 | 0.0184 |
| 4 | 2/5 | 40 | 0.0867 |
| 5 | 3/5 | 60 | 0.0184 |
| 6 | 0/5 | 0 | >0.05 |
| 7 | 2/5 | 40 | 0.0867 |

Protonated/acidified nucleic acids differ greatly in their therapeutic effectiveness against burn wound infection, ranging in this study from 0% (6) to 94% (C2). In all, C and B2 were the most efficacious, with 94% (17/18 C2) and, with 93% (28/30 B2) of the mice responding to treatment ($p<0.0001$ compared to control) followed by I rate ($p<0.001$). Protonated/acidified nucleic acids 2, 3, 5 were moderately efficacious (60% effectiveness), while B7, 4, 7 were marginally effective (40% effectiveness). Protonated/acidified nucleic acid 6 did not appear to show any therapeutic activity in this study.

These protonated/acidified nucleic acids were effective when given either systemically by intravenous and subcutaneous administration, or given locally to the affected site in the skin by topical application. Treatment using these two routes resulted in almost 100% survival rates and complete eradication of the bacteria from infection sites in the livers, spleens and blood. All untreated control mice died from the infection, with high numbers of bacteria recovered from their tissues.

Comparison between B2 and Ciprofloxacin

The efficacy of protonated/acidified nucleic acid B2 for the treatment of burn wound infection was compared to that of ciprofloxacin, a potent fluoroquinolone that has been shown to be efficacious in the treatment of burn wound infection. Protonated/acidified nucleic acid B2 was found to be equally efficacious as ciprofloxacin for the treatment of burn wound infection, with both therapeutic agents resulting in 100% survival rates. The following tables show a comparison of in vivo efficacy of B2 and ciprofloxacin for the treatment of burn wound infection.

| Survival Rates | | | |
|---|---|---|---|
| Antibiotic | No. Survivors/Total Animals | % Survival | p < Control |
| Untreated control | 0/5 | 0 | — |
| Ciprofloxacin | 5/5 | 100% | <0.01 |
| B2 | 5/5 | 100% | <0.01 |

| Microbiological quantitation of tissues | | | | |
|---|---|---|---|---|
| | Average CFU | | | |
| Antibiotic | Blood | Liver | Spleen | Skin |
| Untreated control | $2.3 \times 10e^6$ | $2.1 \times 10e^7$ | $3 \times 10e^6$ | ND |
| Ciprofloxacin | $1.8 \times 10e^5$ | NG | NG | $3 \times 10e^6$ |
| B2 | $1.4 \times 10e^3$ | NG | NG | $2 \times 10e^6$ |

Where NG = no growth,
ND = no data.
Microbiological comparisons of the CFUs in livers, spleens, skin and blood of both treated groups reveal no significant difference in the abilities of the drugs to eradicate these organisms from these infection sites.

Topical Protonated/Acidified Nucleic Acid Treatment of Burn Wound Infection

To determine whether burn wound infection could be effectively treated by protonated/acidified nucleic acids administered topically, mice were infected by topically applying the bacteria into the burn sites on the animals' backs, and treated in the same manner as described above. The following table summarizes the results showing the efficacy of topically applied protonated/acidified nucleic acids for the treatment of burn wound infection induced topically:

| | | Survival Rates | | |
|---|---|---|---|---|
| Protonated/ acidified Nucleic Acids | Protonated/acidified Nucleic Acid Concentration (A/ml) | No. Survivors/ Total | % Survival | $p <$ Control |
| Untreated Control (PBS) | — | 0/10 | 0 | — |
| B2 | 1800 | 9/10 | 90 | <0.01 |
| B2 | 335 | 2/5 | 40 | >0.05 |
| B7 | 1800 | 2/5 | 40 | >0.05 |

| Microbiological quantitation of tissues | | | | | |
|---|---|---|---|---|---|
| Group | Mouse # | Blood | Livers | Spleens | Skins |
| Untreated Control | 1 | ND | $5.5 \times 10e^7$ | NG | ND |
| | 2 | ND | $1.0 \times 10e^6$ | $1.9 \times 10e^8$ | ND |
| | 3 | ND | $2.4 \times 10e^8$ | $5.6 \times 10e^9$ | ND |
| B2 (1800 A/ml) | 1 | NG | NG | NG | $3.9 \times 10e^8$ |
| | 2 | NG | NG | $2 \times 10e^5$ | $4.2 \times 10e^7$ |
| | 3 | NG | NG | NG | $2.1 \times 10e^9$ |

Protonated/acidified nucleic acid B2 administered topically was found to be very effective in the treatment of local burn wound infection, resulting in 90% survival rate, while all untreated control animals infected topically succumbed to the infection. The effectiveness of protonated/acidified nucleic acid administered topically was found to be dependent on drug concentration, decreasing the concentration of the protonated/acidified nucleic acid B2 from 1800 A/ml to 335 A/ml resulted in a sharp decrease in survival rates from 90% to 40%. When the blood, spleens, livers and skins of 3 mice which were treated with B2 (1800 A/ml) were analyzed and compared to that of the untreated controls, it was found that all blood, spleen and two out of three liver samples from the treated group were devoid of any detectable CFUs, in contrast to that of the untreated group which harbored high numbers of bacteria in these tissues.

Example 5

Antibiotic Wound Dressing

A polyester woven multifilament mesh netting having a thickness of 0.020 inch is synthesized according to the method described in U.S. Pat. No. 5,676,967, which is incorporated herein by reference. The netting is synthesized having an average pore size of about 1/32 inch.

An aqueous-based solution of 5% protonated/acidified oligonucleotide having the sequence ACGCGCCATTAT (SEQ ID NO: 9) is prepared according to the method of Example 1. This aqueous solution is coated on the mesh netting and adhered to the fibers of the netting. The coated netting is then subjected to dehydration at about 40° C. Following dehydration, one side of the coated netting is thermally bonded to a 1 mm thick solid polymeric film.

Example 6

Sutures

A solution of protonated/acidified C2 monomer is prepared. The solution contains a 10% solution of C2 monomer in an appropriate carrier, such as sterile water or phosphate buffered saline. A size 2/0 (USP standard) Mersilene.®. PET braided multifilament suture is coated at room temperature with the coating solution using conventional laboratory coating equipment, and the coated suture is subsequently dried in air at elevated temperature to remove the solvent.

Example 7

Adhesives

The antimicrobial-containing adhesive composition of the present invention is manufactured using the following procedure. Acrylic polymers and tackifiers are thoroughly mixed at a temperature of about 121° C. to about 127° C. The adhesive composition includes approximately 17% low molecular weight acrylic polymer (HRJ-4326 from Schenectady International, Inc.), 67% medium molecular weight polymer (HRJ-10127 from Schenectady International, Inc.) along with 16% FLORAL 105 synthetic resin from Hercules, Inc. as a tackifier. Once mixed, the polymers and tackifiers are heated to approximately 154° C. to 157° C. with continued mixing until uniform, followed by cooling to about 65° C. Protonated/acidified oligonucleotide (pH 1.5, sequence ACGCGCCATTAT, SEQ ID NO: 9) is then added to the polymer mixture to a final concentration of 2% and mixed until uniform.

The adhesive composition is then melted and applied to a substrate layer in a thin coating approximately 0.05 mm in thickness. The substrate is a co-polyester surgical drape material such as available from DuPont under the tradename HYTREL. The drape can include a layer of protonated/acidified oligonucleotide applied to the substrate layer on a side opposite that to which the adhesive is applied.

Example 8

Wound Sealant

A unit of blood is withdrawn from a patient in sterile fashion. The blood is collected in a standard sterile blood donor set, using CPDA-1 anticoagulant (Terumo Corporation). The collected blood is connected to a sterile disposable blood processing set manufactured by Electromedics Inc., which is in turn mounted on an ELMD500 Autotransfusion System also by Electromedics. The centrifuge insert (125 ml) is set to rotate at 5600 RPM, generating forces within the blood on the order of 2000 G. The blood is then pumped into the insert at 50 ml per minute.

When the insert is nearly full of packed cells with only a small central core of clear plasma remaining, the blood pump is stopped and the centrifuge speed reduced to 2400 RPM. The exit line leading to the plasma collection bag is closed, the exit line leading to another collection bag is opened, and blood flow is reinstituted at 50 ml/min. The blood entering the centrifuge bowl is again fractionated at the lower centrifugal force, causing the erythrocytes and neutrophils to remain in the centrifuge bowl.

The plasma fraction continues to exit the bowl, carrying with it most of the platelets, monocytes, and lymphocytes into the second collection bag to produce a plasma-buffy coat mixture. Blood continues to be pumped into the bowl such that it is filled with erythrocytes, forcing the central plasma column and entrained formed elements into the exit line. Flow continues until the point where erythrocytes first begin to enter the second collection bag. At that point the blood flow is stopped, the exit line to the bag containing the plasma-buffy coat mixture is clamped, and the centrifuge is stopped.

The plasma collection bag containing the plasma-buffy coat mixture is opened, and the blood pump reversed. The platelet-poor red cells and plasma are directed to a third collection bag. The process is repeated until all the whole blood that had been collected is processed. The reconstituted platelet-depleted whole blood may then be reinfused to the patient.

A sterile assemblage of commonly available blood bag spikes, stopcocks and tubing is constructed such that the platelet bag is connected to a three way stopcock. A second port of the stopcock leads to a 60 cc syringe, and the third leg leads to a 0.25 square meter surface area hemoconcentrator manufactured by Minntech Inc., the outlet of which is in turn connected to a Terumo Corporation sterile blood transfer bag. The plasma-buffy coat mixture is then aspirated into the 60 cc syringe. By adjusting the attached stopcock, the flow path between syringe and hemoconcentrator is opened. A vacuum of −400 torr is applied to the discharge port of the hemoconcentrator, and the plunger of the 60 cc syringe is compressed to force the plasma through the blood path of the hemoconcentrator over about two minutes to produce a plasma-buffy coat concentrate.

The vacuum is immediately disconnected, and the empty 60 cc syringe is replaced by a 20 cc syringe full of normal saline. The saline is immediately infused into the hemoconcentrator to flush residual plasma-buffy coat concentrate from the device into the receiving transfer bag to form the final plasma-buffy coat concentrate. Protonated/acidified nucleic acid (pH 1.5, sequence ACGCGCCATTAT, SEQ ID NO: 9) is then added to the plasma-buffy coat concentrate to a final concentration of 1%.

Example 9

In Vivo Assays

Several examples are provided of in vivo studies to determine the efficacy of the present invention as an antibacterial agent. The following experiments focus on topical skin and the outer ear epidermis, as well as examples of systemic treatment for sepsis.

Efficacy in Topical Skin Bacterial Infections

Skin boils, called furuncles, were treated with protonated/acidified nucleic acids. A furuncle is a localized pyogenic infection typically originating in a hair follicle. A furuncle is a round, tender, pus-filled area of the skin, developing a white cap which will rupture if stressed. Often, a furuncle may be an infection of the hair follicle in the deepest section. A furuncle will normally heal in 10-25 days. Without treatment, furuncles usually must drain before they will heal. This most often occurs in just under 2 weeks. If the furuncle is a deep lesion, it may require systemic antibiotic therapy to eliminate the bacteria in addition to minor surgery to open the furuncle and drain the pus. In summary, furuncles are painful swellings of the skin caused by deep skin infection with bacteria, that rarely resolve untreated in less than 10 days.

Protonated/Acidified Nucleic Acids' Efficacy in Treatment Of Staphylococcal Furuncles Protonated/acidified nucleic acids have demonstrated efficacy in treating a 1.5 cm furuncle on the back of a 36-year-old male subject in good health. Within 8 hours, the protonated/acidified nucleic acids rapidly and dramatically relieved both the pain and swelling of the furuncle.

Protonated/acidified nucleic acid (pH 1.5, sequence ACGCGCCATTAT, SEQ ID NO: 9) was used to treat a 1.5 cm furuncle one day after its appearance. The nucleic acid consisted of 2'-O-methyl substituted ribonucleotides, phosphodiester linked, end blocked with an inverted T at both the 5' and 3' ends. Specifically, 100 µl of protonated/acidified nucleic acids were dissolved in water (18.9 mMolar) to treat the 1.5 cm furuncle, which was raised, red and swollen, with a 2-3 mM pustule, and was very painful to the subject. After 8 hours of treatment, the furuncle had spontaneously drained and was significantly reduced to approximately 0.5 cm in size with a concurrent reduction in swelling and redness. The subject's pain was significantly alleviated. A second 50 µl application of protonated/acidified nucleic acids was applied at this time.

After 16 hours from the initial treatment, there was virtually no swelling, pain, or inflammation. A small pinkish area of <0.5 cm remained from the original furuncle. A final application of protonated/acidified nucleic acids was applied, 24 hours post treatment of the infection, to continue accelerating the healing process. The residual vestiges of the furuncle healed on their own after the third application and within a day.

In conclusion, protonated/acidified nucleic acids have been demonstrated to be very effective in rapidly treating a Staphylococcal furuncle and using water as the transport medium. Protonated/acidified nucleic acids were particularly effective in rapidly resolving both the pain and swelling of the furuncle.

Efficacy in Topical Treatment of Ear Infections

Protonated/acidified nucleic acids were very effective in treating outer ear epidermal infections in chinchillas caused by *Pseudomonas aeruginosa* bacteria. All the chinchilla infected ears that received continued protonated/acidified nucleic acid treatment were completely cured 4 days after treatment began.

Chinchillas' ears were infected with *Pseudomonas aeruginosa* bacteria. Specifically, the maceration of the epidermal layer of the chinchillas' ears was caused by prolonged exposure of the ears to water. This helps create a receptive environment for the Pseudomonas infection in the epidermal layer of skin lining in the chinchillas' ear canals. Cotton plegets were saturated with a suspension of washed *Pseudomonas aeruginosa* and were inserted in the ear canals of the chinchillas. The plegets were removed after 48 hours.

Treatment of the chinchillas began on day 3 post infection, when the ears were judged to have a "level 3" severity as determined by otoscopic examination. The chinchillas received two daily topical applications of either 400 µl of protonated/acidified nucleic acids at pH 1.5 of sequence ACGCGCCATTAT, SEQ ID NO: 9, in water (2.8 mMolar) or 400 µl of the protonated/acidified nucleic acids of identical sequence (2 mMolar) in a vehicle mixture (water/ethanol/propylene glycol). The nucleic acid consisted of 2'-O-methyl substituted ribonucleotides, phosphodiester linked and end blocked with butanol at both the 5' and 3' ends. The chinchillas were examined daily to assess the effectiveness of treatment based on the degree of severity of the ear infections.

The results of the protonated/acidified nucleic acid treatment indicated that all of the treated chinchillas' ears showed a significant reduction in the severity of ear infections, as determined by otoscopic examination. Significant improvements could be observed after 3 treatments of protonated/acidified nucleic acids. The chinchillas received treatment for an additional 4 to 5 days. Untreated control chinchillas showed no improvement over this time frame. In contrast, all ear infections that received continued protonated/acidified nucleic acids treatment were completely cured by day 7 post infection (i.e., 4 days after treatment began with protonated/acidified nucleic acids).

In addition, there were slight differences in the progression of healing between protonated/acidified nucleic acids dissolved in the two transport mediums, water or the vehicle mixture (water/ethanol/propylene glycol). Based on otoscopic examination, protonated/acidified nucleic acids in the vehicle mixture were slightly more effective in treating the ear infections.

In conclusion, protonated/acidified nucleic acids have demonstrated effectiveness in treating chinchillas' outer ear infections caused by *Pseudomonas aeruginosa*. This is significant since this infectious bacteria is naturally an antibiotic-resistant bacteria.

Efficacy in Treatment of Strep. pyogenes Skin Infection on a Dog

A 135 lb. 2 year old, female Newfoundland had sustained a cut on her abdomen and developed a Strep. pyogenes infection. The area was swollen, inflamed and painful to the touch. Treatment with Neosporin.®. (Warner-Lambert, Co.) for 3 days failed to produce any improvement. Two treatments, separated by 12 hours, directly to the injury with 2'-O-methyl substituted ribonucleotides that were phosphodiester linked, pH 1.5, end blocked with butanol at both the 5' and 3' ends, with sequence of ACGCGCCATTAT (SEQ ID NO: 9), completely cleared up the infection, swelling, inflammation, and sensitivity to touch.

Protonated/Acidified Nucleic Acid Efficacy in a Topical Pseudomonas Burn Model of Infection Protonated/acidified nucleic acids have demonstrated efficacy in treating topical skin infections in immuno-compromised mice. Mice were treated with cyclophosphamide (200 mg/kg, I.P.) in advance of a burn to the skin to inhibit their immune systems. Three days later burns were induced, followed by application of $10^9$ CFU of *Pseudomonas aeruginosa* topically applied to the burn site to create an infection. Treatment with nucleic acid occurred at 4 hrs. and 8 hrs. post infection. The nucleic acid used in the experiment was at pH 1.5, had the sequence ACGCGCCATTAT, SEQ ID NO: 9, and consisted of 2'-O-methyl substituted ribonucleotides, phosphodiester linked and end blocked with butanol at both the 5' and 3' ends. One hundred percent (100%) of the treated animals survived and were free of systemic Pseudomonas infections while 90% of the control animals developed systemic infections and died. The protonated/acidified nucleic acids were able to cure the topical infection. In addition, topical application of nucleic acids were able to prevent the topical Pseudomonas infection from progressing to a fatal, systemic infection.

Protonated/Acidified Nucleic Acid Efficacy in a Systemic Pseudomonas Burn Model of Infection Mice were treated S.C. with $10^6$ or $10^7$ CFU of *Pseudomonas aeruginosa* after induction of a skin burn. Two hours post infection, treatment was initiated with acidified nucleic acid. Forty percent (40%) of the dose was administered I.V. with the remainder given S.C. The nucleic acid used in the experiment was at pH 1.5, had the sequence ACGCGCCATTAT, SEQ ID NO: 9, and consisted of 2'-O-methyl substituted ribonucleotides, phosphodiester linked and end blocked with butanol at both the 5' and 3' ends. The procedure was repeated 6 hrs. later. Additional subcutaneous injections were given twice daily on day two and three. All of the 45 control animals died, and 100% of the 40 treated mice survived and were healthy. These treated, healthy mice were sacrificed and checked for sepsis. Pseudomonas bacteria were not detected in the spleen, liver, or blood.

In conclusion, a protonated/acidified nucleic acid was 100% effective at treating a systemic Pseudomonas infection that would have been fatal if left untreated.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A method of treating a wound comprising applying to said wound a composition comprising an antibacterial formulation comprising a protonated/acidified nucleic acid of up to 23 nucleotides, wherein said protonated/acidified nucleic acid comprises a backbone structure modified from that of naturally occurring nucleic acids, and wherein said protonated/acidified nucleic acid has a pH of about 1.0 to about 4.0 when dissolved in water, wherein said composition inhibits the growth of pathogenic bacteria in said wound, wherein said pathogenic bacteria is selected from the group consisting of *Staphylococcus aureus, Pseudomonas aeruginosa, Streptococcus pyogenes, Staphylococcus* spp., *Streptococcus mutans, Escherichia coli*, and *Klebsiella pneumonia*, thereby treating said wound.

2. The method of claim 1, wherein said protonated/acidified nucleic acid is a monomer.

3. The method of claim 2, wherein said monomer comprises a blocking chemical modification at the 5' position of the monomer and a blocking chemical modification at the 3' position of the monomer.

4. The method of claim 1, wherein the formulation of said protonated/acidified nucleic acid is from about 0.1 to about 5 percent of the dry weight of the composition.

5. The method of claim 1, wherein said composition is applied topically, intravenously, or subcutaneously to said wound.

* * * * *